United States Patent [19]

Provell

[11] Patent Number: 5,002,068

[45] Date of Patent: Mar. 26, 1991

[54] SHIELDING AND FOCUSING OF MAGNETIC FIELDS

[75] Inventor: Gregory J. Provell, Somerset, N.J.

[73] Assignee: Biomagnetics Systems, Inc., Newark, N.J.

[21] Appl. No.: 380,873

[22] Filed: Jul. 17, 1989

[51] Int. Cl.[5] .......................... A61F 5/37; A61F 5/56

[52] U.S. Cl. .................................... 128/846; 128/849

[58] Field of Search ............................... 128/849-856, 128/798, 802, 908, DIG. 18, 846

[56] References Cited

U.S. PATENT DOCUMENTS

| | | | |
|---|---|---|---|
| 3,310,053 | 3/1967 | Greenwood | 128/846 |
| 4,604,998 | 8/1986 | Bellina | 128/849 |
| 4,901,738 | 2/1990 | Brink | 128/849 |
| 4,938,233 | 7/1990 | Orrison, Jr. | 128/849 |

*Primary Examiner*—Robert A. Hafer
*Assistant Examiner*—Michael Brown
*Attorney, Agent, or Firm*—William R. Moran

[57] ABSTRACT

A method is provided for shielding humans and inanimate subjects from magnetic fields. The method includes, in part, interposing between the subjects and the source of a magnetic field, at least one second magnetic field disposed in such a manner that the polarity of the second magnetic field cancels or at least partially neutralizes the magnetic strength of the first magnetic field. The second magnetic field can also be disposed so as to permit only a portion of the first magnetic field to escape shielding and thereby focused in a predetermined direction. Devices which normally emit magnetic energy and containing the shielding of the present invention are also provided.

10 Claims, 1 Drawing Sheet

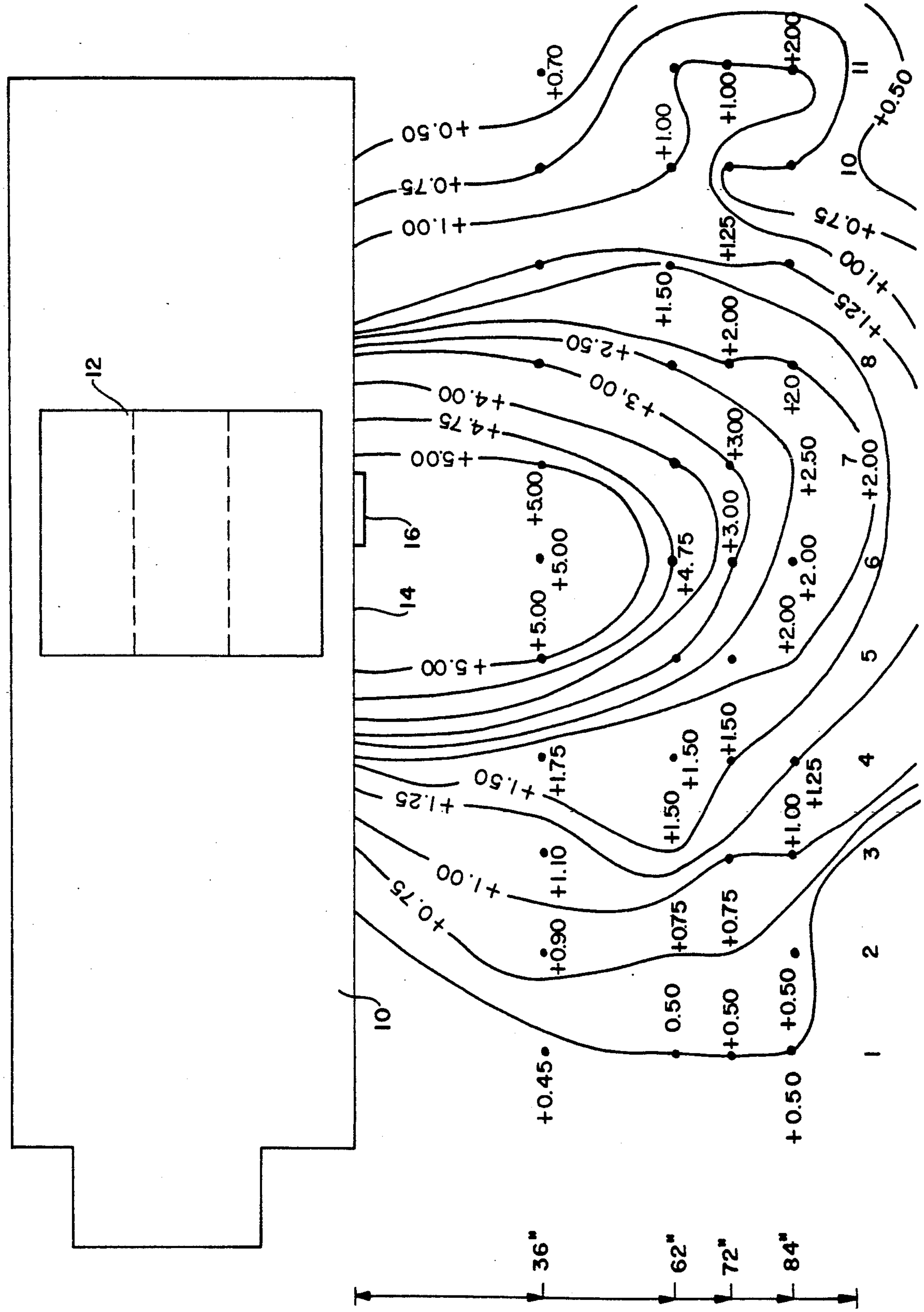
10
12
14
16
+0.50
+0.75
+1.00
+1.25
+1.50
+2.00
+2.50
+3.00
+4.00
+4.75
+5.00
+0.70
+0.45
+0.90
+1.10
+1.75
+0.75
0.50
+0.50
1
2
3
4
5
6
7
8
10
11
36"
62"
72"
84"

SHIELDING AND FOCUSING OF MAGNETIC FIELDS

BACKGROUND OF THE INVENTION (1) Field of the Invention

This invention relates in general to magnetic energies. In one aspect, this invention is directed to shielding of human and inanimate subjects from magnetic fields. In a further aspect, this invention is related to a method for shielding humans from electromagnetic fields such as those generated by transmission lines, magnetic resonance imaging devices and the like. In another object, this invention is directed to the utilization of such shielding to focus electromagnetic energy. A still further object is to provide devices equipped with such shielding.

(2) Description of the Related Art

Recently there has been a rising concern by scientists and an increasing awareness on the part of the public in general, of the potential health hazards of electromagnetic fields. The scientific evidence is increasing daily which indicates that exposure to magnetic fields might conceivable cause adverse health effects in the cells of the human body. A comprehensive background paper was recently issued by the Congressional Office of Technology Assessment which was prepared by a team at Carnegie Mellon University and which indicated that the emerging evidence no longer allows one to categorically assert that there are no risks associated with electromagnetic fields radiated by cables, wires, fixtures and appliances in general. Although scientist have generally assured the public that there was no danger to health, the uncertainty engendered by often contradictory data causes some degree of concern.

Moreover, while the electromagnetic, fields radiated by fixtures and appliances found in the home or workplace may be of a relatively low level, more sophisticed equipment such as transmission lines, large electrical transformers, as well as the more recent magnetic resonance imaging devices, which radiate greater magnetic field strengths, are undoubtedly of greater concern. Magnetism and its effects have been widely discussed in the past and it is evident that magnetic energy does indeed effect the living organism such as humans and agricultural products.

A wide variety of methods have been reported in the literature which are directed to the use of magnetic energy as a diagnostic technique and also for the treatment of diseases in warm blooded animals including humans. For example, magnetic energy has been utilized quite successfully over the past several years to promote the formation of osteoblasts in conjunction with the healing of bone fractures. In many instances markedly improved results in healing times have been achieved by the application of magnetic energy to the site of bone fractures and other injuries.

In U.S. Pat. No. 3,337,776, which issued Aug. 22, 1967, there is disclosed an apparatus for generating magnetic fields which are indicated to be particularly useful for biomedical applications. Although the patentee is not specific as to individual applications, he does state that magnetic fields generated by the apparatus can decrease metabolism values and reacts on the spastic syndrome.

A magnetic probe is disclosed and claimed in U.S. Pat. No. 3,664,327 which issued May 23, 1972 and states that the probe can be employed in relatively inacessable locations, such as in body cavities of animals to cause relaxation of muscle tissue.

A magnetic medical treatment device is disclosed in U.S. Pat. No. 3,921,620 which states that the effects of a magnetic field upon a living body are due to the fact that the electrolyte within the living body is dissociated by polarization and induced currents and is effective in controlling the sympathetic nervous system.

On May 3, 1977, U.S. Pat. No. 4,020,590 issued to A. R. Davis and discloses an apparatus and method for treating seeds in a unipolar magnetic field. It is indicated in the patent that this treatment enhances the germination rate of the seeds, as well as providing plants having greater sugar content, increased protein and other desirable features.

In U.S. Pat. No. 4,134,395 which issued Jan. 16, 1979 also to A. R. Davis, a method is disclosed and claimed which uses magnetic fields for clinical examination of animals to determine damaged, diseased, abnormal or malfunctioning parts of the body. Changes in tensioning and relaxation of the body extremities are an indication of body abnormalities.

A method for treating cancer is disclosed in U.S. Pat. No. 4,622,952 which issued Nov. 18, 1986 and which involves timing an electromagnetic energy to the resonant energy absorption frequencies of the intracellular structures of the selected cells and then exposing a subject to this tuned electromagnetic energy field. The field can also be tuned to the frequency which has been calculated to be closest to to the resonant frequency of the cancer cells and furthest from the normal cells.

U.S. Pat. No. 4,622,953, which issued to the same patentee, disclosed the identical procedure for the treatment of atherosclerotic lesions. In this process, metabolic and activity varying substances such as ferric hydroxide and dextran were employed and by applying the proper resonant energy, the heat in the diseased cell is increased by an increment sufficient to kill the diseased cell but not sufficient to kill normal cells.

In a patent issued to Robert T. Gordon on May 5, 1987, U.S. Pat. No. 4,602,359, a process is described and claimed for the treatment of cancer in a host organism which comprises providing to the host organism minute particles capable of being inductively heated and which are of a size which can be absorbed into cancer cells. Thereafter the organism is subjected to an alternating electromagnetic field to heat the particles at that point in metabolic time when the maximum difference in magnetic susceptability between the cancer cells and normal cells within the reagion occurs, and then continuing the inductive heating to increase intracellular temperature to selectively kill the cancer cells.

The common belief over the years relating to magnets has been that the two magnetic poles, north and south, are homogeneous and that they emanate the same potential type of energy. This belief has been found to be a misconception since the two poles of a magnet are in fact totally different in electric potential and effect, and accordingly the application of the respective poles to living systems has been found to produce quite different results.

The north pole, which is defined as the north seeking pole, is now believed to provide a negative form of energy while the south pole, which is defined as the north-seeking pole, is believed to provide a positive form of energy. It has also been found upon examination of the electron paths associated with the fields surrounding the respective poles that the south pole end of a magnet provides a right hand spin of electrons, i.e., a clockwise rotation of electron movement, as contrasted with the north pole electron spin, which provides a left hand spin or counterclockwise rotation of its electron field.

It has been further observed that the lines of magnetic energy leave the south pole to re-enter the magnet at the Bloch Wall where the 180 degree phase takes place, and leave the Block Wall at that point to go on as the north pole energy to re-enter the magnet at its north pole.

It is also believed that magnetic energy has an effect on cells such as blood cells, nerve tissue cells and the like. Cells are deemed to be bioelectric in nature, function and behavior. Moreover, Due to the orientation of such cells and of the metal elements and other ions contained therein, the blood cells have been found to decrease certain biological effects when exposed to the north pole and to increase other biological effect when exposed to the magnetic south pole. This same type of reaction has been noted in connection with the other type cells of the body, it having been observed that, as a general matter, the application of north pole energies to an existing unhealthy or abnornmal condition tends to have an arresting, quieting or relaxing effect, to induce an overall healing reaction akin to the body's own defense mechanism. On the other hand, the application of south pole energies tends to have a strengthening, activating effect, which has been found useful in treating some abnormal conditions, particularly those associated with a slowing or weaking in function. A more detailed description of magnetic pole energies can be found in Davis et àl, *Magnetism and its Effects On the Living System*, Acres U.S.A., Kansas City, Mo. (1974) and Davis et al, *The Magnetic Effect*, Exposition Press, Inc. (1975).

It is therefore evident that magnetic energies do indeed have an effect upon plants and living organisms, and which in some instances may be detrimental.

Surveys of magnetic resonance imaging devices and other types of equipment capable of producing appreciable magnetic fields were performed in order to determine the polarity and intensity of magnetic fields in areas where there are potentials of both occupational exposure and exposure to members of the general public.

Preliminary investigations regarding biological effects of exposure to magnetic fields had indicated a polarity dependence. Cancer cells exposed to the North field showed a significant decrease in the number of surviving cells after a period of incubation, whereas the same type cells exposed to the South field indicated a measurable increase in the number of surviving cells compared to the unexposed controls.

Considering the potential significance of this phemomenon, exposure to the South field from devices radiating such energy should be as low as is reasonably achievable.

Accordingly, one or more of the following objects will be achieved by the practice of this invention. It is an object of this invention to provide a method for shielding human and inanimate objects from magnetic fields. Another object is to provide a shielding for humans from electromagnetic fields such as those generated by transmission lines, magnetic resonance imaging devices and the like. A further object of the invention is to provide devices equipped with appropriate shielding. These and other objects will readily become apparent to those skilled in the art in the light of the teachings herein set forth.

SUMMARY OF THE INVENTION

In its broad aspect this invention is directed to a method for shielding humans and inanimate subjects from magnetic fields. The method comprises, in part, interposing between the subjects and the source of a magnetic field, at least one second magnetic field disposed in such a manner that the polarity of the second magnetic field cancels or at least partially neutralizes the magnetic strength of the first magnetic field. The second magnetic field can also be disposed so as to permit only a portion of the first magnetic field to escape shielding and thereby focused the magnetic energy in a predetermined direction. Devices which normally emit magnetic enegy and containing the shielding of the present invention are also provided.

BRIEF DESCRIPTION OF THE DRAWING

The single figure is a schematic drawing looking down on the top of a mobile trailer housing a magnetic resonance imaging unit. The electromagnetic field radiating to the outside of the trailer is depicted at different locations.

DETAILED DESCRIPTION OF THE INVENTION

As indicated above, the present invention is directed to a method of shielding magnetic energy radiating or emanating from a magnetic source. Using the shielding in accordance with the procedure of this invention can greatly reduce or even eliminate any potential danger from a magnetic field, especially energy from a South field.

While it has not been established with certainty, the current views seem to tend towards the possibility that magnetic fields, especially the South magnetic field may adversely effect living organisms. It is with this in mind that the present invention was conceived in order to reduce or eliminate exposure of humans and inanimate objects to unecessary magnetic energy. While many of the devices used in the home today emit little magnetic energy, there are other devices wherein exposure to their magnetic field may have adverse consequences.

Since there are few if any materials which can not be penetrated by magnetic energy, it was found that the best way to reduce or eliminate unwanted magnetic energy was to utilize a separate and opposing magnetic field to counteract the energy of the first magnetic source. Accordingly, it was found that by using one or more magnets of a lesser strength, but located and oriented in a set fashion, the undersirable effect of the first magnetic source could be counteracted.

Since the magnetic field strength weakens in proportion to the distance away from the magnetic source, it was found that a magnet of a relative low strength if properly placed could effectively eliminate unwanted radiation. As noted in Examples 1-5 which follow, a shield of a lesser strength placed at a predetermined distance from the magnetic source, was effective in completely neutralizing the magnetic energy.

It has been found that the second magnetic field which comprises the shield, can be fabricated from a wide variety of materials and in a wide variety of configurations. For example, ferrite particles or powders can be embedded in a variety of plastic or other materials which can then be made into a wide variety of shapes and sizes. When such materials are rendered magnetic, then can serve as excellent shields for use in the method of the present invention. Such materials can be obtained from the Fermag Company of Edison, N.J. in various strengths of their magnetic fields. For example, magnetic shielding can be obtained having magnetic field strengths of from about 1000 to about 1500 gauss and higher. The actual strength needed will of course be determined by the strength of the magnetic source and the proximity of the shielding to the source.

As indicated, the shielding can be fabricated in a wide variety of shapes and sizes as well as thicknesses. In many instances, using the shield in the form of sheets will be sufficient and such sheets can be arranged in several layers one behind the other if necessary. In other instances, it may be necessary to have the shield configured into a cylindrical, spherical or other shape in order to provide the optimum shielding of the first magnetic source. Additionally, while the shielding can be a magnetized material, it is also possible to have the shielding be an electromagnet whose power is derived from an electrical source.

Measurement of the field strength of the first magnetic source and of the second magnetic source or shielding, can be done with a gaussmeter such as Model 5-0-5, which can be obtained from the Annis Company of Indiana. Also, a magnetometer is available from the Albert Roy Davis Research Laboratory, of Green Cove Springs, Fla. To identify the poles using this device, the side or end of the magnet is brought up to the meter. If the needle moves to the right (+), it is the South pole energy that is being measured. If the needle moves to the left (−) it is the North pole of the magnet.

The distance between the magnetic source and the meter varies with the magnetic strength. For this magnetometer, ½ inch is about 150 Gauss; 1 inch, 200 Gauss; 1 and ½ inch 300 Gauss, 2 and ½ inches 500 Gauss; 5 inches, 1800 Gauss; 9 inches, 3500 Gauss; 12 inches 4500 Gauss; and the like. Although different gaussmeters will have different scales, the data obtained with one meter will be relative to the different field strengths for the particular magnets tested and the distance of the meter from the magnetic source.

In general, it has been observed that the energy radiating from the South pole is the energy which might have adverse effects on humans. Thus, by utilizing a shield in accordance with the teachings of this invention wherein this South pole energy is neutralized, humans can be protected from such adverse effects.

The following examples are illustrative of the present invention.

EXAMPLES 1-5

In order to demonstrate that a source of magnetic energy can be adequately shielded, a magnet having a field strength of approximately 3500 gauss was placed in a flat surface. A magnetic shield in the form of a sheet was placed about six inches from the surface of the magnet which radiated a south (+) field. The magnetic shield employed was obtained from the Fermag Company of Edison, N.J. and was comprised of magnetic ferrite embedded in a pliable substrate material. The shield was in the form of a flat sheet of no greater than 0.25 inches in thickness and had a magnetic strength of 1200 gauss. The shield was placed vertically so that its flat surface was parallel to the magnet and yet perpendicular to the magnetic field radiating therefrom. The shield was oriented so that its south (+) field faced the magnet.

The strength of the magnetic field was measured using a gaussmeter (Model 5-0-5, obtained from the Annis Company of Indiana and placed about 9.5 inches from the magnet ( about 3.5 inches behind the shield when the shield was in place). The measurements obtained are set forth below in Table I.

TABLE I

| | Gaussmeter Reading | |
|---|---|---|
| Example | Unshielded | Shielded |
| 1 | +4.00 | +0.5 |
| 2 | +4.50 | 0.0 |
| 3 | +5.0 | 0.0 |
| 4 | +5.0 | +0.5 |
| 5 | +5.0 | +1.0 |

EXAMPLE 6

A survey was made at a large northeast research institution and indicated that fairly high intensities of magnetic fields could be detected in areas adjacent to various devices. This prompted a survey of an operating mobile magnetic resonance imaging unit to determine whether high levels of magnetic energy was being emitted from such a unit. An examination of the console regularly occupied by the staff personnel in the room housing the MRI magnets, showed that the intensity levels were substantially higher and areas of both positive (South field) and negative (North field) were measured. This unit was a 0.3 Tesla Hybrid Resisture magnet with magnetic bricks. The field polarity is obviously determined by the configuration of the components.

Substantial levels were measured outside of the trailer housing the unit which also was posted with a sign indicating "Magnet Hazard". In the single drawing, there is depicted a schematic top view of the trailer 10, showing the approximate location of the magnet 12, of the MRI unit and the side 14, from which actual measurements of the field strengths were made. Warning sign 16, was on the outer trailer wall at approximately the location of the MRI unit inside. The scale on the side of the drawing is in inches measured away from the side of the trailer.

It is evident from the data obtained that there is substantial magnetic radiation from the side of the MRI mobile unit and which is the less desirable positive type of radiation. Although there is no correlation yet available to connect the intensity of the magnetic field with any detrimental effects on humans, the mere fact that the mobile unit contains the "Magnet Hazard" warning sign on the trailer should be sufficient to encourage using an appropriate shielding. The particular unit for which the measurements were made, was located on a city street where pedestrians would pass through the field depicted in the drawing.

Although the invention has been illustrated by the preceding examples, it is not to be construed as being limited to the materials employed therein, but rather, the invention is directed to the generic area as herein before disclosed. Various modifications and embodiments of the invention can be made without departing from the spirit or scope thereof.

What is claimed is:

1. A method for shielding a human or inanimate subject from a magnetic field emanating from a first source, which process comprises interposing between said subject and said first source, a second magnetic field emanating from a second source, said second source being disposed with respect to the orientation of the first source, so that the polarity of the second magnetic field is such as to counteract at least some of the magnetic field strength emanating from said first source.

2. The method of claim 1 wherein the strength of the magnetic field emanating from said first source is substantially greater than the strength of the magnetic field emanating from said second source.

3. The method of claim 1 wherein the magnetic field emanating from said first source is an electromagnetic field.

4. The method of claim 1 wherein the first source is a magnetic resonance imaging device.

5. The method of claim 2 wherein the magnetic field strength emanating from the first source is greater than the magnetic field emanating from the second source by a factor of at least about 10 to 1.

6. The method of claim 5 wherein said second source is located at a sufficient distance from the first source so that the magnetic field strength of the second source is sufficient to counteract the field strength emanating from said first source.

7. The method of claim 1 wherein said second source has natural magnetic properties.

8. The method of claim 1 wherein said second source has electromagnetic properties.

9. A device comprised of a first source which radiates mangetic energy and containing thereon a shield comprised of a second magnetic field emanating from a second source, said second source being disposed with respect to the orientation of the first source, so that the polarity of the second magnetic field is such as to counteract at least some of the magnetic field strength emanating from said first source.

10. A method of focusing a magnetic field radiating from a first source which comprises shielding some of the magnetic field from said first source with one or more second magnetic fields emanating from one or more second source, said second source being disposed with respect to the orientation of the first source, so that the polarity of the second magnetic field is such as to counteract at least some of the magnetic field strength emanating from said first source and the non-shielded magnetic energy is focused in a predetermined path.

* * * * *

UNITED STATES PATENT AND TRADEMARK OFFICE
CERTIFICATE OF CORRECTION

PATENT NO. : 5,002,068

DATED : March 26, 1991

INVENTOR(S) : Walter C. Rawls Jr., and Gregory J. Provell

It is certified that error appears in the above identified patent and that said Letters Patent is hereby corrected as shown below:

On title page, item [75] should read:

"Inventors: Walter C. Rawls Jr., Jacksonville, FL; and Gregory J. Provell, Somerset, NJ "

Item [19] should read --Rawls, Jr. et al--

Signed and Sealed this

Twenty-second Day of December, 1992

*Attest:*

DOUGLAS B. COMER

*Attesting Officer* *Acting Commissioner of Patents and Trademarks*